United States Patent [19]

Bernard et al.

[11] Patent Number: 5,712,367
[45] Date of Patent: Jan. 27, 1998

[54] PROCESS FOR THE SOLUBILIZATION OF PEPTIDES AND PROCESS FOR PEPTIDE SYNTHESIS

[75] Inventors: Jean-Marie Bernard, Mornant; Kamel Bouzid, Lyon; Christian Gervais, Villeurbanne, all of France

[73] Assignee: Rhone-Poulenc Chimie, Courbevoie, France

[21] Appl. No.: 329,674

[22] Filed: Oct. 25, 1994

Related U.S. Application Data

[63] Continuation of Ser. No. 103,306, Aug. 9, 1993, abandoned, which is a continuation of Ser. No. 998,757, Dec. 30, 1992, abandoned, which is a continuation of Ser. No. 592,028, Oct. 2, 1990, abandoned.

[30] Foreign Application Priority Data

Oct. 2, 1989 [FR] France .................. 89 13054

[51] Int. Cl.$^6$ .................................................. C07K 1/02
[52] U.S. Cl. ............... 530/338; 530/333; 530/335; 530/344; 530/345
[58] Field of Search ................ 530/333, 338, 530/344, 345

[56] References Cited

U.S. PATENT DOCUMENTS

| | | | |
|---|---|---|---|
| 3,700,609 | 10/1972 | Tregear et al. | 260/2.5 R |
| 4,156,683 | 5/1979 | Lehn | 540/465 |
| 4,379,764 | 4/1983 | Fujii | 260/112.5 |
| 4,418,012 | 11/1983 | Fujii | 260/112.5 |
| 4,436,874 | 3/1984 | Aspisi et al. | 525/327.1 |
| 4,532,212 | 7/1985 | Odell | 435/197 |
| 4,857,656 | 8/1989 | Kouge | 558/271 |
| 5,047,573 | 9/1991 | Bradaczek et al. | 530/338 |

FOREIGN PATENT DOCUMENTS 0 017 536  10/1980  European Pat. Off.

OTHER PUBLICATIONS

Narita et al., Prediction and Improvement of Protected Peptide Solubility in Organic Solvents, Int. J. Peptide Protein Res. 24, 580–587 (1984).

Gross et al., The Peptides; Analysis, Synthesis, Biology, Academic Press 1, 45–64 (1979).

Fuhrhop et al., Organic Synthesis, 4.1.2 Peptides, Verlag Chemie, 207–220 (1983).

Aboderin, JACS 87, 5469, 1965.

Jones, J Chem Soc C, 436, 1968.

Stewart, Aust J Chem 18, 1699, 1965.

Bodansky, *Princ of Pept Synth* (Springer–Verlag) pp. 69–81, 1984.

Johnson *J Org Chem* 33 4521, 1968.

Aboderin *J Am Chem Soc* 87, 5469 1965.

Schwyzer et al., Helv. Chim Acta, vol 49, 134–158 (1966).

Beyerman et al., Rec. Trav. Chim. Pays Bas (Recueil) vol. 92, 481–492 (1973).

Bayer et al., Nature, vol. 237, 512–513 (1972).

Merrifield, J. American Chemical Society, vol. 85, 2149–2154 (1963).

Tsukube, J. Chem. Soc. Perk. Trans I (1982) 2359–2363.

Gross & Meiengofer, *The Peptides* vol. 2 (Academic Press, 1980) 294–328.

*Primary Examiner*—David Likton
*Attorney, Agent, or Firm*—Finnegan, Henderson, Farabow, Garrett & Dunner, L.L.P.

[57] ABSTRACT

A process is disclosed for making peptides soluble in a water-immiscible organic solvent, comprising linking a lipophilic group with an amide or ester bond to the terminal carboxyl group of said peptide; when the lipophilic group is linked to L-serine, a molecule is obtained with a solubility in water at 25° C. of less than 30 g/liter. This lipophilic group is non-polymeric and chemically defined. A process is also disclosed for the synthesis of peptides, optionally protected, in a liquid medium, wherein the starting material is an amino acid or peptide made soluble in an organic medium by a lipophilic group A—L linked to the carboxyl function of the starting amino acid or peptide, and are added to amino acids or peptides to be condensed which are activated on their acid function and protected on their amine function and are optionally protected on their side chain. The peptides resulting from the synthesis are used, where appropriate, for the synthesis of medicinal products, vaccines or agri-foodstuff or plant-protection.

21 Claims, No Drawings

PROCESS FOR THE SOLUBILIZATION OF PEPTIDES AND PROCESS FOR PEPTIDE SYNTHESIS

This application is a continuation of application Ser. No. 08/103,306 filed Aug. 9, 1993, now abandoned; which is a continuation of application Ser. No. 07/998,757 filed Dec. 30, 1992, abandoned; which is a continuation of application Ser. No. 07/592,028 filed Oct. 2, 1990, abandoned.

The present invention relates to a process for solubilization of peptides. It also relates to a liquid-phase process for peptide synthesis.

A large number of peptide synthesis methods are described in the literature. They all have basic points in common, such as:

protecting the side-chain function of an amino acid with a protective group which can be cleaved upon completion of a synthesis of the peptide, protecting the (N∝) amide function of the amino acid with a protective group which can be cleaved after condensation of the amino acid, and activating the carboxylic acid function of the protected amino acid and then condensing the latter with an amino acid or peptide whose C-terminal function is protected and whose amine function is free;

obtaining the peptide by complete "deprotection" of the protective groups after condensation of all the amino acids.

The various methods of synthesis are distinguished by the physical state of the phase in which the synthesis takes place: liquid phase or solid phase.

The so-called liquid-phase methods of synthesis carry out all the reactions in a homogeneous phase.

In the method described by Bodansky and de Vigneaud in the Journal of American Chemical Society 81, 5688–5691 (1959), the starting amino acid is protected with a methyl group and the successive amino acids are condensed "stepwise" after protection of their amine function with a benzyloxycarbonyl group and activation of their carboxyl function by a nitrophenyl ester. The successive intermediates are purified by precipitation or washes. This technique requires a high number of difficult or lengthy synthesis steps which inevitably lead to a substantial loss of products. Schwyzer and Sieber (Helvetica Chemica Acta, 49, 134–158, 1966) obtained a yield of ACTH of only 6.85% using this technique.

The synthesis described by Beyermann et al. (Rec. Tray. Chim. Pays Bas 92,481, 1973) consists of applying the same method as above, starting with an amino acid or peptide whose carboxyl group is protected with a benzyl group, and in carrying out the couplings in the presence of an excess of protected amino acid anhydride so as to increase the yields. The number of operations is as numerous as in the above process, and the peptide formed often loses its solubility in an organic medium as soon as the number of amino acids exceeds four or five.

Some liquid-phase methods of synthesis employ more sophisticated protective agents solubilizing the starting amino acid or peptide; European Patent No. 0,017,536 mentions the phenylazobenzylsulphonylethyloxy (OPSE) group as a protective group. This group enables the peptides formed to be solubilized in dimethylformamide and to be rendered insoluble both in water and in other organic solvents. The synthesis is still carried out "stepwise" with precipitation of each peptide intermediate formed before the addition of a further amino acid, which creates problems in relation to the filtration of the solids. This process, like all the processes mentioned above, does not permit peptides having a large number of amino acids to be maintained in solution.

Among liquid-phase processes, processes in which the amino acid is maintained in solution by the use of a non-crosslinked linear polymer such as polyethylene glycol may also be mentioned (Mutter and Bayer, Nature 237, 512 (1972)), with the by-products being removed by ultracentrifugation or precipitation.

Among so-called solid-phase methods of synthesis, the technique described by Merrifield in 1963 in the Journal of American Chemical Society 85, 2149–2154, which consists of binding the C-terminal carboxyl function of the first amino acid or first peptide group to an insoluble support, may be mentioned. The couplings and washes may be standardized so as to render the process capable of automation. This technique still remains highly expensive to date, since it is necessary to use the reactants in large excess so as to convert all the peptide chains undergoing synthesis in a reasonable time. The purity and homogeneity of the peptides formed is still far from ideal; the by-products consisting of incomplete peptide chains must be removed at the end of the reaction. In effect, purification during the intermediate state is impossible, and even at the final stage it is difficult since it requires complicated equipment and a sophisticated and hence expensive technique, such as preparative high pressure liquid chromatography.

Extrapolation of this technology to the industrial level remains a problem unsolved to date, on account of the difficulties in working with large amounts of resins, either in a stirred reactor or in a fixed bed.

DESCRIPTION OF THE PREFERRED EMBODIMENTS

The present invention solves a majority of the problems in the prior art.

A process for the solubilization of peptides making it possible to carry out their synthesis in a non-aqueous liquid phase and their purification has now been found.

In one embodiment, the present invention provides a process for making peptides, which are optionally protected or salified, soluble in a water-immiscible organic solvent comprising linking the C-terminal carboxyl group of said peptide via an amide or ester bond to a non-polymeric lipophilic group. When the lipophilic group is linked to L-serine, a molecule is obtained with a solubility in water at 25° C. of less than about 30 g/liter. This lipophilic group is non-polymeric and chemically defined below.

The lipophilic group which will make it possible to carry out peptide synthesis in a water-immiscible organic liquid phase is preferably composed of two entities A and L, linked to one another by a covalent bond and linked covalently to the carboxy function of the peptide via the entity A:

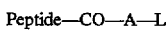

Peptide—CO—A—L

The group —CO— is a C-terminal carboxyl group of the peptide.

The reaction for attaching the lipophilic group to a peptide or amino acid may be represented as follows:

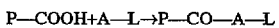

P—COOH+A—L→P—CO—A—L wherein P—COOH represents an amino acid or peptide.

The entity —A— is a bifunctional anchoring linker or spacer between the peptide undergoing synthesis and the group L.

When used for making individual amino acids soluble in a water-immiscible solvent, the process may be represented by the following reaction (Q—COOH represents an amino acid):

$$Q\text{—COOH} + A\text{—}L \rightarrow Q\text{—CO—}A\text{—}L.$$

The group —L— is the lipophilic portion of the entity A—L. In no case is this group L polymeric. It is preferably a hydrocarbon group, optionally containing halogen. It corresponds to the general formula:

$$\text{—}C_{(a)}H_{(b)}O_{(c)}N_{(d)}S_{(e)}Si_{(f)}X_{(g)}$$

in which:

a is an integer between 1 and 50 b is an integer between 3 and 101 c is an integer between 0 and 6 d is an integer between 0 and 2 e is an integer between 0 and 2 f is an integer between 0 and 2 g is an integer between 0 and 20

X is a halogen selected from fluorine, chlorine and bromine

Among all the compounds which can be represented by the group L, preferably (a) is an integer above 6, and still more preferably above 12, and (g) is preferably an integer above 2.

The group A which, as specified above, represents the bifunctional anchoring linker or spacer, preferably contains at one end at least one alcohol or amine function (B) and at the other end a carbonyl function or an ether function. The group A is represented by the following general formula:

$$B\text{—}R_1\text{—}Ar_{(k)}\text{—}(R_2\text{—}\underset{\underset{O}{\|}}{C}_{(n)}\text{—}O_{(m)})_p$$

in which:

B is a hydroxyl or amino group;

Ar is a mono- or polycyclic aromatic radical;

$R_1$ is selected from a covalent bond, an alkylene radical containing 1 to 4 carbon atoms, optionally substituted with an aryl radical such as a phenyl radical, and an alkylenecarbonyl group;

$R_2$ is selected from a covalent bond, an alkylene radical containing 1 to 4 carbon atoms, optionally substituted, an oxyalkylene group containing 1 to 4 carbon atoms in the alkylene chain and an oxygen atom;

k, m and n are integers equal to 0 or 1, wherein at least m or n must be 1; and p is an integer equal to 1 or 2.

The two entities A and L can also form a single group corresponding to the formulae:

$$B\text{—}R_1\text{—}Ar' \text{ or } B\text{—}CH_{(3-q)}\text{—}Ar''(q)$$

in which:

B and $R_1$ are the same as above;

Ar' is a polycyclic aromatic radical; and

Ar" is a benzene radical and q is an integer equal to 2 or 3.

Among the groups A—, the groups of the following formulae may be mentioned:

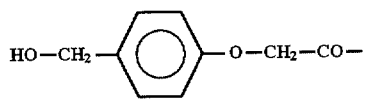
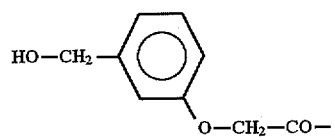
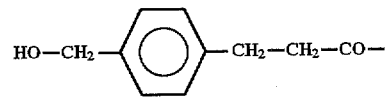
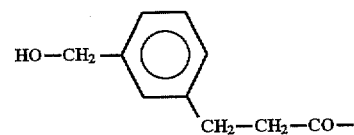
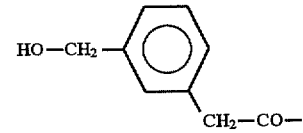
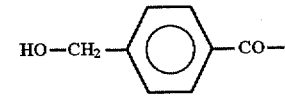
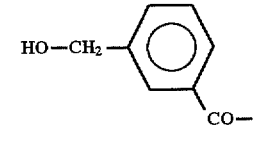
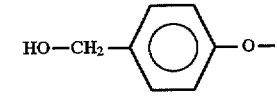
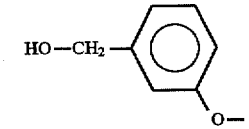
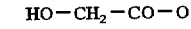
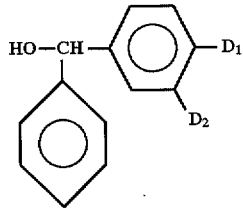

in which:

$D_1$ and $D_2$ are identical or different groups selected from the radicals or atoms O; CO; $CH_2O$; $CH_2CO$; OCO; and H; except that $D_1$ and $D_2$ cannot both be H;

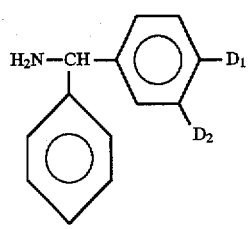
in which $D_1$ and $D_2$ are the same as above;
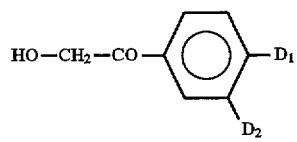
in which $D_1$ and $D_2$ are the same as above.
Among the lipophilic groups —L, the groups of the following formulae may be mentioned:
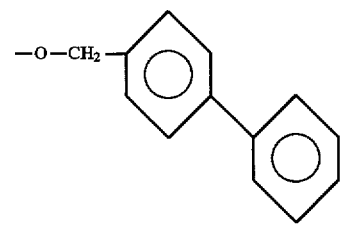
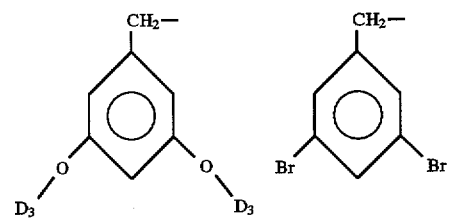
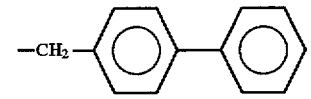
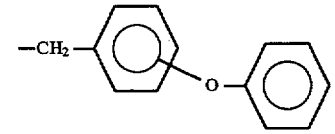
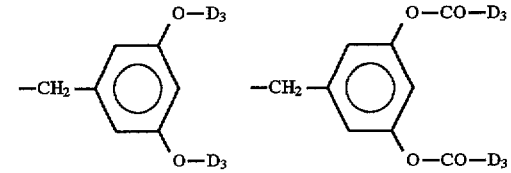
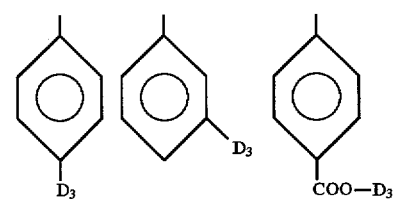
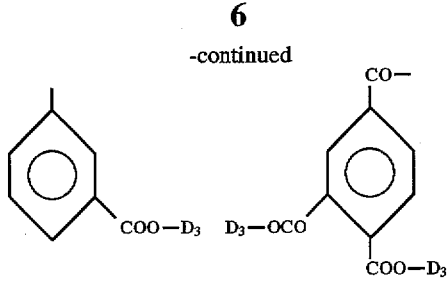
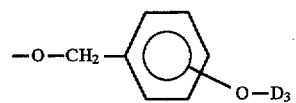
in which formula $D_3$ is an alkyl radical having 1 to 12 carbon atoms;
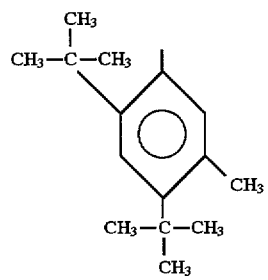
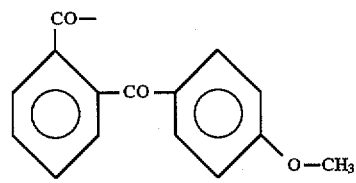
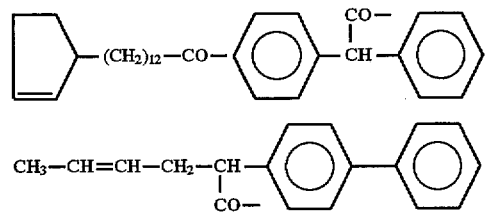
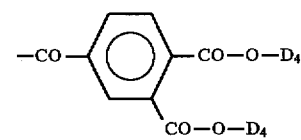
in which $D_4$ is an aryl or aralkyl group;
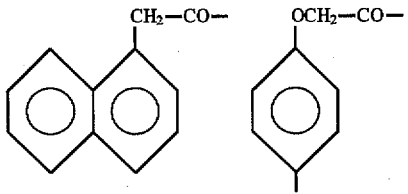
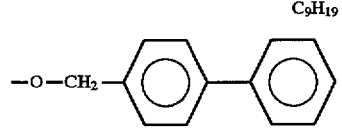

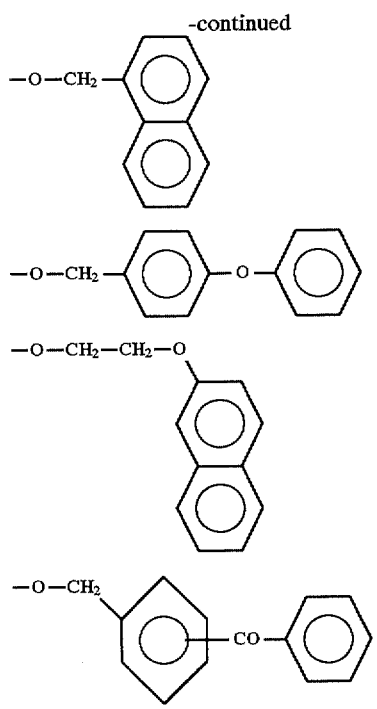

Solvents in which the peptides are solubilized as a result of their binding to the lipophilic group are preferably water-immiscible organic solvents such as halogenated aliphatic derivatives, especially methylene chloride, aromatic derivatives such as anisole or chlorobenzene and esters such as ethyl acetate.

The solubilization process enables the solubility of the peptides in an organic phase to be significantly increased. It enables, for example, homogeneous solutions of a concentration greater than or equal to about 50 g/liter to be obtained.

Another advantage of the present process originates from the fact that the peptides linked to the lipophilic groups A—L defined above have a high partition coefficient in favor of the organic phase when settling takes place in the presence of water.

This property is advantageous for purifying the peptides by aqueous washes.

The present invention also relates to a process for the synthesis of peptides, optionally protected, in a liquid medium, wherein the starting material is an amino acid or a peptide made soluble in an organic medium by a lipophilic group A—L as defined above. This lipophilic group is linked to the carboxyl function of the starting amino acid or peptide. This linking step may be represented by the following reaction:

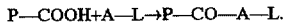

The starting materials are then added to the amino acids or peptides to be condensed (P'COOH). These amino acids or peptides to be condensed are activated on their amino acid function and protected on their amine function and are optionally protected on their side chain.

The protection of the amine function of the amino acids may be accomplished by the replacement of a hydrogen atom of this function by a group such as tertbutyloxycarbonyl by the formation of DANE salts, for example by reaction of the amine function with a betadicarbonyl compound.

The activation of the N-protected peptide or amino acid is carried out by the formation either of a mixed anhydride by means of an acid chloride, or of a mixed anhydride by means of alkyl chloroformate, or of a symmetrical anhydride by means of carbodiimide, or of an activated ester according to a conventional synthesis technique, or by any other technique of activation of an N-protected amino acid.

An advantage of the present process is that it permits a productive and repetitive synthesis in an organic medium in which the peptide linked to the lipophilic molecule A—L, defined above, is always maintained in solution. Each peptide —A—L intermediate, N-protected or otherwise, is maintained as soluble in the organic medium.

Another important advantage of the process is that it enables the excess reactants and the by-products of the synthesis to be removed from the organic phase by simple washing with water;

after the condensation step, the products such as the excess activated amino acids or activated peptides, the salts, acids or alcohols or all the other by-products of the reaction which are not linked to the synthesized peptide chain;

after the deprotection step, the agents for unblocking the desired functions and the by-products of the cleavage reaction of the N-protective group.

This process thus avoids all the steps of purification by precipitation, which are necessary in the prior art.

Monitoring of the purity of the peptide undergoing synthesis is possible at any time, by simple sampling and analysis by any technique such as high performance liquid chromatography, proton or carbon nuclear magnetic resonance, potentiometry, mass spectrometry, etc.

As a result of the similarity of the condensation and deprotection operation, when each of the amino acids is added, the process of the present invention enables peptides to be synthesized according to a repetitive procedure.

As a result of the repetitive nature of the synthesis, the process may be advantageously carried out in an automated form.

Finally, when the synthesis of the initial sequence of the peptide is complete, the peptide is freed from its protective groups and from the solubilizing group A—L by hydrolysis or hydrogenolysis or by any other deprotection method used in peptide synthesis.

This process is especially advantageous for the synthesis of hydrophilic peptides or peptides bearing hydrophilic groups, such as, for example, those which contain the following amino acids in their chain: arginine, glutamine, asparagine, serine, threonine, glycine.

The peptides resulting from the synthesis are used, where appropriate, for the synthesis of medicinal products, vaccines or agri-foodstuff or plant-protection products.

The present invention will be described more fully by means of the following examples, which are not to be considered as limiting the invention.

I. —SYNTHESIS OF THE REAGENTS ENABLING THE SOLUBILIZING GROUPS A—L TO BE OBTAINED

Example 1

Preparation of 4-phenylbenzyl 3(chloromethyl)benzoate

The following were introduced successively into a 500-cm$^3$ three-necked round-bottomed flask:

40 g (0.217 mol) of biphenylmethanol 150 cm$^3$ of toluene 42.9 g (0.227 mol) of 3-(chloromethyl)benzoyl chloride.

The mixture was stirred and heated to 40° C.

25 cm³ of N-methylmorpholine (0.227 mol) was then added in the course of 10 minutes.

The temperature of the reaction medium rose spontaneously to 60° C., then the medium was heated to 80° C. for 2 hours and 30 minutes.

The final reaction mixture was poured into a separating funnel, diluted to 1 liter by adding ethyl acetate and then washed successively with 450 cm³ of normal hydrochloric acid and 400 cm³ of normal aqueous sodium hydrogen carbonate solution, then with water to neutrality.

Distillation of the solvents led to a solid residue which was crystallized from hot to cold in 1.6 liters of methanol.

4-Phenylbenzyl 3-(chloromethyl)benzoate was obtained in an 81% yield (59.5 g), in the form of a white solid having a melting point of 102° C.

Its structure was established by mass spectrometry and proton NMR (360 MHz).

Analysis by thin-layer chromatography (TLC) on Merck silica 60° F. 254 plates revealed a single spot in each of the two eluent systems tested:

ethyl acetate/cyclohexane (2/5) Rf=0.7 hexane/acetone (4/1) Rf=0.6.

Examples 2 to 14

By working according to the same procedure as in Example 1, the following compounds were prepared:

Example 2

3-Phenoxybenzyl 3-(chloromethyl)benzoate

Appearance: oil
Yield: 94%

Example 3

9-Methyleneanthryl 3-(chloromethyl)benzoate

Appearance: solid having a melting point of 148° C. (recrystallation in methanol)
Yield: 82%

Example 4

4-Phenylbenzyl 3-(bromomethyl)benzoate

Appearance: solid having a melting point of 63°–65° C.
Yield: 26%

Example 5

4-tert-Butylbenzyl 3-(chloromethyl)benzoate

Appearance: oil
Yield: 47%

Example 6

2,4-Dichlorobenzyl 3-(chloromethyl)benzoate

Appearance: solid having a melting point of 75° C. (recrystallization in acetone+water)
Yield: 75%

Example 7

Choloesteryl 3-(chloromethyl)benzoate

Appearance: solid having a melting point of 122° C. (recrystallization in dichloromethane+methanol)
Appearance: 78%

Example 8

Phytyl 3-(chloromethyl)benzoate

Appearance: oil
Yield: 53%

Example 9

2,2,3,3,4,4,4-Heptafluorobutyl 3-(chloromethyl)benzoate

Appearance: oil
Yield: 79%

Example 10

2,2,3,3,4,4,5,5,6,6,7,7,8,8,8-Pentadecafluoroocytl 3-(chloromethyl)benzoate

Appearance: oil
Yield: 81%

Example 11

Cholesteryl chloroacetate

Appearance: crystals
Yield: 72%

Example 12

2,2,3,3,4,4,4-Heptafluorobutyl chloroacetate

Appearance: liquid of boiling point 80° C. (under 2660 Pa)
Yield: 20%

Example 13

2,2,3,3,4,4,5,5,6,6,7,7,8,8,8-Pentadecafluorooctyl chloroacetate

Appearance: oil
Yield: 72%

EXAMPLE 14

4-(3,5-dichlorophenoxy)benzyl chloroacetate

Appearance: oil
Yield: 97%

II. —SYNTHESIS OF VARIOUS PROTECTED AMINOACYL-A—L OR PEPTIDE-A—L SPECIES

Example 15

Synthesis of N-tert-butyloxycarbonyl-L-leucine [4-(hydroxymethyl)biphenyl 3-methylbenzoate] ester:

The following were introduced successively into a 500-cm³ three-necked round-bottomed flask:

15 g of N-tert-butyloxycarbonyl-L-leucine potassium salt (equivalent to 0.056 mol), 180 cm³ of dry DMF, 14.905 g (equivalent to 0.044 mol) of 4-(hydroxymethyl) biphenyl 3-(chloromethyl)benzoate dissolved in 100 cm³ of dry DMF, and 1.5 g of sodium iodide.

The mixture was brought to 75° C. with stirring.

After 2 hours of reaction, 490 cm³ of ethyl acetate were added.

The organic solution was washed successively, twice with 100 cm³ of water, 200 cm³ of dilute KHCO₃ solution (pH 8.5), 200 cm³ of water, 200 cm³ of KHSO₄ solution (pH 2) and 200 cm³ of water.

The organic phase was dried over Na₂SO₄, then filtered and evaporated to give an oil with a yield equal to 100%.

The structure of the product was confirmed by mass spectrometry and by proton NMR (360 MHz).

Analysis by thin-layer chromatography on silica plates revealed a single spot in the following elution system: ethyl acetate/hexane (2/5) Rf=0.66.

Example 16 to 22

By working according to the same procedure as in Example 15, the following compounds were prepared:

Example 16

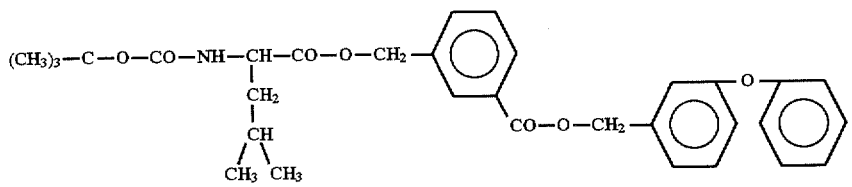

Appearance: oil
Yield: 98%

Example 17

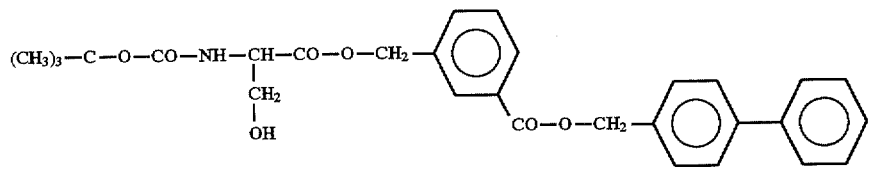

Appearance: oil
Yield: 95

Example 18

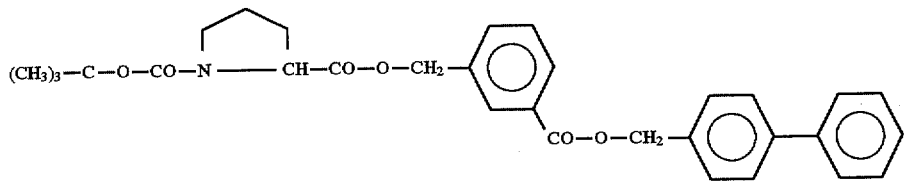

Appearance: oil

Yield: 100%

Example 19
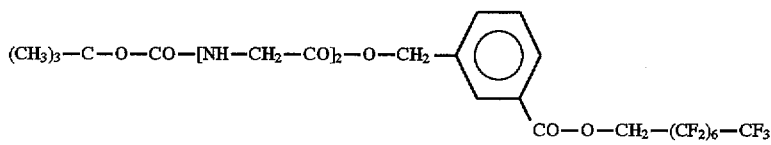
Appearance: white powder
Yield: 100%
Melting point: 215° C.
Example 20
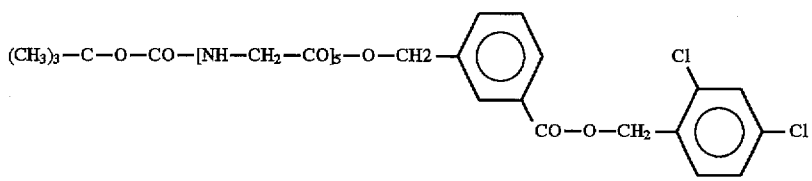
Appearance: white powder
Yield: 77.5
Example 21
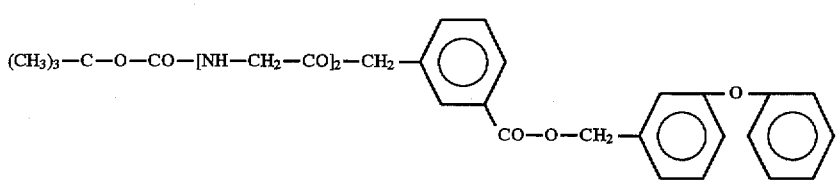
Appearance: oil
Yield: 100%
Example 22
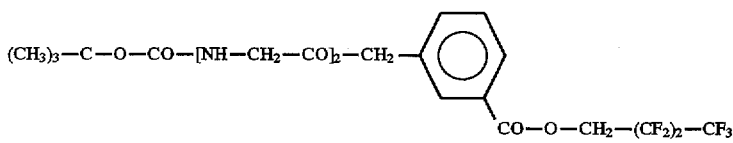
Appearance: powder
Yield: 70%
Example 23
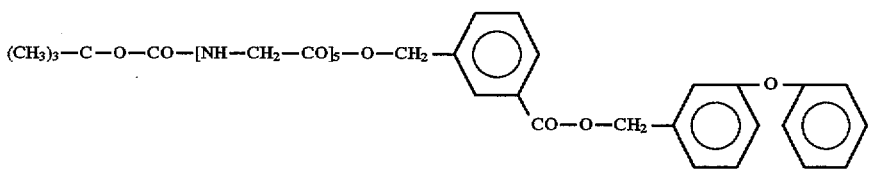
Appearance: white powder
Example 24

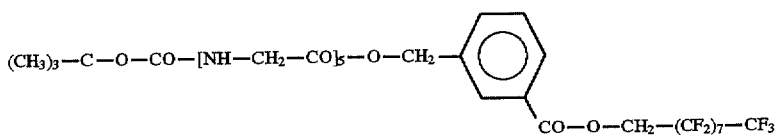

Appearance: white powder
Melting point: 240° C.

Example 25

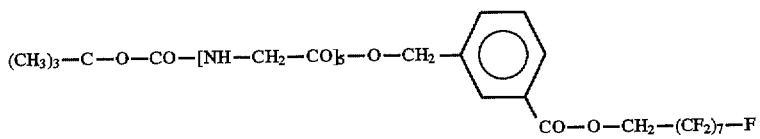

Appearance: white powder

III. —SYNTHESIS OF VARIOUS AMINOACYL-A—L SPECIES

Example 26

Synthesis of L-leucine [4-(hydroxymethyl)biphenyl 3-methylbenzoate] ester hydrochloride:

The following were introduced successively into a 250-cm³ three-necked round-bottomed flask:

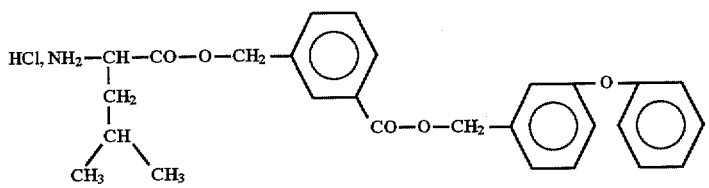

24.6 g (equivalent to 0.044 mol) of N-tert-butyloxycarbonyl-L-leucine [4-(hydroxymethyl)biphenyl 3-methylbenzoate] ester, 100 g of dichloromethane.

A stream of dry hydrochloric acid was then bubbled into the stirred mixture for 1 hour 30 minutes at room temperature.

The solution was then outgassed under a stream of nitrogen for 20 minutes.

The reaction mixture was then evaporated to a volume of 50 cm³ and the product was thereafter precipitated by adding 200 cm³ of ethyl ether.

The product obtained after filtration weighed 19.3 g (0.0413 mol) (94% yield). It was a white powder having a melting point of 121°–122° C.

The structure of the product was confirmed by mass spectrometry and by proton NMR (360 MHz).

Analysis by thin-layer chromatography on silica plates revealed a single spot in the following eluent system: dichloromethane/methanol/acetic acid (90:10:5) Rf=0.55.

Examples 27 to 29

By working according to the same procedure as in Example 26, the following compounds were prepared:

Example 27

Appearance: oil

Yield: 98

Example 28

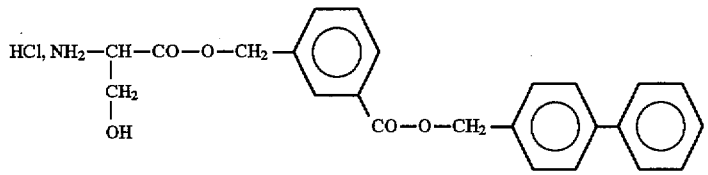

Appearance: white powder
Yield: 98%

Example 29

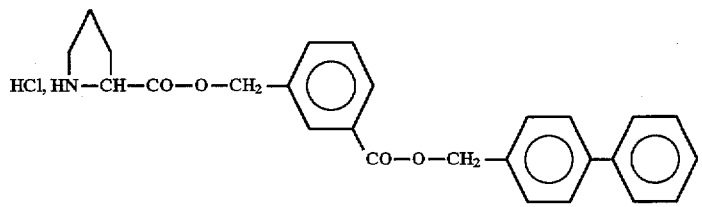

Appearance: white powder
Yield: 80%

IV. —MEASUREMENT OF THE SOLUBILITIES OF THE MOLECULES OF FORMULA (L)-SERYL-A—L IN WATER

Example 30

The lipophilic groups A—L, when they were linked to L-serine, gave a molecule with a solubility in water of less than 30 g/l at room temperature.

Synthesis of the molecules of formula (L)-seryl-A—L

The hydrochlorides of formula HCl, (L)-seryl-L—A, obtained according to the method described in Examples 26 to 29, were dissolved in dichloromethane. Ammonia gas was passed into this solution at room temperature. The ammonium chloride precipitate obtained was rapidly filtered off. The filtrate was then concentrated under greatly reduced pressure. The product obtained after concentration was immediately ground in water for 15 minutes at room temperature and then filtered off.

The solubility of the product of formula (L)-seryl-A—L was measured in the filtrate.

Solubility of the molecules of formula L)-seryl-A—L

L-Serine [4-(hydroxymethyl) biphenyl 3-(hydroxymethyl) benzoate] ester:
  solubility in water at 25° C.: 0 g/l (insoluble) L-Serine [benzyl 3-(hydroxymethyl)benzoate] ester:
  solubility in water at 25° C.: 0.2 g/l L-Serine [3-phenoxybenzyl 3-(hydroxymethyl)benzoate] ester:
  solubility in water at 25° C.: 0.75 g/l
By way of comparison:
L-Serine methyl ester:
  solubility in water at 25° C.: >100 g/l L-Serine benzyl ester:
  solubility in water 25° C.: >100 g/l

V. —SOLUBILIZING EFFECTS IN ORGANIC SOLVENTS OF THE LIPOPHILIC GROUP PROTECTING THE CARBOXYL FUNCTION OF THE PEPTIDES

The solubilizing effect of the lipophilic group was demonstrated by the solubility measurements described below, where the model peptide was an especially hydrophilic peptide: N-tertbutyloxycarbonylpentaglycine.

$(CH_3)_3-C-O-CO-(NH-CH_2-CO)_5-OR$

| | Solubility in g/100 cm$^3$ | | | Partition coefficient between CH$_2$Cl$_2$ |
|---|---|---|---|---|
| R | anisole | CH$_2$Cl$_2$ | H$_2$O | and H$_2$O |
| R1 | 5 | >10 | 0.0016 | >1,000 |
| R2 | 5 | >10 | 0.0008 | >2,000 |
| —CH$_3$* | insoluble | 0.33 | 0.50 | 0.66 |
| benzyl* | insoluble | 0.070 | 0.017 | 4.1 |

*by way of comparison

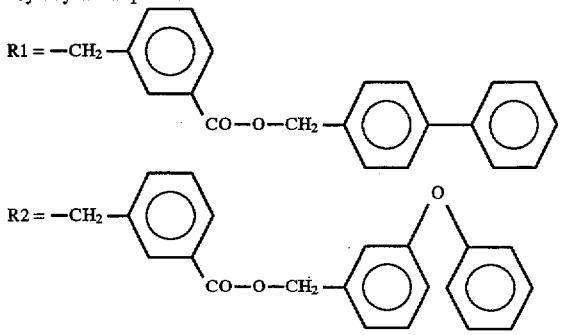

VI. —PEPTIDE SYNTHESIS IN A CONCENTRATED ORGANIC MEDIUM BY MEANS OF LIPOPHILIC GROUPS A—L

The pentapeptide leucine enkephalin L-tyrosyl-glycyl-glycyl-L-phenylalanyl-L-leucine was synthesized:

with the [4-(hydroxymethyl)biphenyl 3-methylbenzoate] ester as the lipophilic group A—L;
with a tert-butyloxycarbonyl group as the group protecting the amine function of the constituent amino acids.

Example 31

Example 31a:
Synthesis of N-tert-butyloxycarbonyl-L-phenylalanyl-L-leucine [4-(hydroxymethyl)biphenyl 3-(hydroxymethyl) benzoate] ester.

The following were introduced successively into a 500-cm³ three-necked reactor:
10.33 g (0.039 mol) of N-tert-butyloxycarbonyl-L-phenylalanine,
75 cm³ of dichloromethane.

After dissolution, the temperature of the reaction medium was lowered to −5° C. and 4.29 cm³ of N-methylmorpholine (0.039 mol) and 4.46 cm³ of pivaloyl chloride (0.036 mol) were added successively with stirring.

After a reaction time of 4 hours, 14.018 g (0.030 mol) of L-leucine [4-(hydroxymethyl)biphenyl 3-(hydroxymethyl) benzoate] ester hydrochloride and then 3.3 cm³ of N-methylmorpholine (0.030 mol) were added.

After a reaction time of 2 more hours, the reaction mixture was washed successively with:
2×25 cm³ of water (pH 5.8–6.44),
3×30 cm³ of dilute KHCOs (pH 8.2–8.3),
2×30 cm³ of water (pH 7.3–7.2),
2×30 cm³ of H₂SO₄ (pH 3.89–3.35),
2×30 cm³ of dilute NaCl (pH 6.7–6.5).

The yield of product, assayed relative to a standard, was
Analysis by thin-layer chromatography on silica plates revealed a single spot in the following eluent system: ethyl acetate/hexane (2:5) Rf=0.38.

The structure of the product was verified by mass spectrometry and by proton NMR (360 MHz) and its purity was confirmed by analysis by high performance liquid chromatography (HPLC).

Example 31b:
Synthesis of L-phenylalanyl-L-leucine [4-(hydroxymethyl)biphenyl 3-(hydroxymethyl) benzoate] ester hydrochloride The solution obtained after extraction in Example 31a was dried by distilling off the dichloromethane under vacuum. The final volume was brought to 150 cm³.

At room temperature, a stream of dry hydrochloric acid was bubbled into the solution for 1 hour 45 minutes. The reaction mixture was then outgassed by bubbling dry nitrogen for 1 hour into the solution.

The reaction mixture was concentrated under vacuum to a volume of 75 cm³.

Thin-layer chromatography on silica plates confirmed the purity of the product: Rf=0.8 in the eluent system dichloromethane/methanol (90:10).

Analysis by HPLC. confirmed that cleavage of the N-tertbutyloxycarbonyl group was quantitative (100%).

A sample of the product precipitated in the system ethyl acetate/ethyl ether had a melting point of 167°/169° C.

Example 31c:
Synthesis of N-tert-butyloxycarbonylglycyl-glycyl-L-phenylalanyl-L-leucine [4-(hydroxymethyl)biphenyl 3-(hydroxymethyl)benzoate] ester.

The following were introduced successively into 500-cm³ three-necked reactor:
5.1 g (0.022 mol) of N-tert-butyloxycarbonylglycyl-glycine,
75 cm³ of dichloromethane.

After dissolution, the temperature of the reaction medium was lowered to −5° C. and 2.4 cm³ of N-methylmorpholine (0.022 mol) and 2.7 cm³ of pivaloyl chloride (0.0176 mol) were added successively with stirring.

After a reaction of 2 hours with stirring at −5° C., one half of the solution obtained in Example 31b of L-phenylalanyl-L-leucine [4-(hydroxymethyl)biphenyl 3-(hydroxymethyl) benzoate] ester hydrochloride (0.0147 mol in 40 cm³ of dichloromethane) and then 1.62 cm³ of N-methylmorpholine (0.0147 mol) were added.

After a reaction time of 2 hours 30 minutes more with stirring, the reaction mixture was washed successively with:
30 cm³ of dilute H₂SO₄ (pH 3.5),
2×30 cm³ of water (pH 4.5–3.6),
2×30 cm³ of dilute NaOH (pH 8.6–7.3),
2×30 cm³ of water (pH 6.8–6.1).

Analysis by thin-layer chromatography on silica plates revealed a single product in the following eluent system: dichloromethane/methanol (90:10) Rf=0.6.

The structure of the product was verified by mass spectrometry and by proton NMR (360 MHz) and its purity was confirmed by analysis by high performance liquid chromatography (HPLC).

Example 31d:
Synthesis of glycyl-glycyl-L-phenylalanyl-L-leucine[4-(hydroxymethyl)biphenyl 3-methylbenzoate] ester hydrochloride.

The solution obtained after extraction in Example 31c was dried by distilling off the dichloromethane under vacuum. The final volume was brought to 75 cm³.

At room temperature, a stream of dry hydrochloric acid was bubbled into the solution for 1 hour 30 minutes. The reaction mixture was then outgassed by bubbling dry nitrogen into the solution for 1 hour.

The yield of product, assayed from the solution thereby obtained, was 100%.

The purity of the product was verified by thin-layer chromatography on silica plates and by HPLC.

Example 31e:
Synthesis of N-tert-butyloxycarbonyl-L-tyrosyl-glycyl-glycyl-L-phenylalanyl-L-leucine [4-(hydroxymethyl) biphenyl 3-methylbenzoate] ester.

The following were introduced successively into a 250-cm³ three-necked reactor:
5.26 g of N-tert-butyloxycarbonyl-L-tyrosine,
40 cm³ of dichloromethane.

After dissolution, the temperature of the reaction medium was lowered to −15° C. and 2.23 cm³ of N-methylmorpholine (0.02 mol) and 2.5 cm³ of isobutyl chloroformate (0.019 mol) were added successively with stirring.

After a reaction time of 10 minutes, this solution was added to the solution obtained in Example 31d of glycyl-glycyl-L-phenylalanyl-L-leucine [4-(hydroxymethyl) biphenyl 3-methylbenzoate] ester hydrochloride (0.0135 mol in 40 cm³ of dichloromethane) with stirring at −15° C.; a further 1.5 cm³ of N-methylmorpholine (0.0135 mol) were then added.

After a reaction time of 4 hours more with stirring, the reaction mixture was washed successively with:
50 cm³ of dilute H₂SO₄ (pH 6.6),
25 cm³ of dilute H₂SO₄ (pH 2.2),
2×40 cm³ of water (pH 4.3–3.8),
40 cm³ of dilute KHCO₃ (pH 8.1), 2×40 cm³ of water (pH 7.9–6.9).

The organic phase was dried by evaporation to dryness to give 14.4 g of a white solid of meringue-like appearance.

Analysis by thin-layer chromatography on silica plates revealed a single product.

The structure of the product was verified by mass spectrometry and by proton NMR (360 MHz) and its purity was confirmed by analysis by high performance liquid chromatography (HPLC).

Example 31f:

Synthesis of N-tert-butyloxycarbonyl-L-tyrosyl-glycyl-glycyl-L-phenylalanyl-L-leucine.

In a 100 cm³ three-necked round-bottomed flask, 5 g of N-tert-butyloxycarbonyl-L-tyrosyl-glycyl-glycyl-L-phenylalanine-L-leucine [4-(hydroxymethyl)biphenyl 3-methylbenzoate] ester were suspended in 15 cm³ of methanol.

15.7 cm³ of N sodium hydroxide and 15 cm³ of acetonitrile were added.

After a reaction time of 4 hours, 20 cm³ of ethyl ether were added.

The aqueous phase was separated after settling has taken place and washed with 2×20 cm³ of ethyl ether, and then acidified to pH 3 with 5% strength $KHSO_4$ solution.

The N-tert-butyloxycarbonyl pentapeptide was extracted with a 75:5 ethyl acetate/ethyl ether mixture.

The organic phase (75 cm³) was washed with 2×30 cm³ of water (pH 4.0–5.0).

The final organic phase was diluted to 100 cm³ in a volumetric flask for assay by HPLC. relative to a pure reference standard.

The yield assayed after extraction and saponification was 94.5% relative to the L-leucine [4(hydroxymethyl)biphenyl 3-methylbenzoate] ester hydrochloride, which means that the yield obtained for each step was greater than 99%.

After assay, the organic solution was concentrated and dried at very low pressure. The residue obtained (3.5 g, equivalent to a 100% yield) was dissolved in isopropyl alcohol and was then precipitated by adding diisopropyl ether.

This operation was repeated a second time to give, finally, 2.42 g of a powder, equivalent to a 71% yield of pure isolated product.

The purity of the product was verified by HPLC analysis, by proton NMR spectrometry (360 MHz) and by mass spectrometry.

Example 31g:

Production of L-tyrosyl-glycyl-glycyl-L-phenylalanyl-L-leucine trifluoroacetate.

In a 50-cm³ three-necked round-bottomed flask, 2.12 g (2.78 mmol) of N-tert-butyloxycarbonyl-L-tyrosyl-glycyl-glycyl-L-phenylanalyl-L-leucine, prepared in Example 31f, were dissolved at room temperature in 10 cm³ of a 50:50 (by volume) dichloromethane/anisole mixture and 5 cm³ of trifluoroacetic acid.

After a reaction time of 1 hour with stirring, the solution was concentrated under reduced pressure.

The product was assayed relative to a 100% pure reference standard.

The yield after cleavage was 100% (2.78 mmol of product assayed).

The assayed solution was lyophilized to give 1.72 g of a white powder: final yield of product recovered, 92.5% relative to the N-tert-butyloxycarbonyl-L-tyrosyl-glycyl-glycyl-L-phenylalanyl-L-leucine.

The purity of the product was verified by HPLC analysis, by proton NMR spectrometry (360 MHz) and by mass spectrometry.

The elemental analysis of the final product was: C=53.1% H=5.7% N=9.9% F=8.1% for an empirical formula:

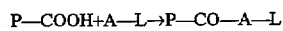

What is claimed is:

1. A process for temporarily rendering a peptide or amino acid soluble in a water-immiscible organic solvent comprising the steps of:
   a) coupling, in a water-immiscible organic solvent, an amino acid or peptide with a lipophilic substituent to form a reaction product P—CO—A—L, according to the following reaction:

P—COOH+A—L→P—CO—A—L wherein
   P—COOH represents an amino acid or peptide, and
   L represents a non-polymeric lipophilic group which bears a linking moiety A, subject to the proviso that A and L together contain at least 18 carbon atoms, and wherein said process the C-terminal carboxyl group of said amino acid or peptide is bonded via ester or amide linkage to the group A—L in the reaction product, and wherein said reaction product is soluble in said water-immiscible organic solvent to the extent of at least 50 g/L;
   b) washing the reaction product P—CO—A—L of step (a) with a neutral, acidic, or basic aqueous solution while said reaction product remains dissolved in the water-immiscible organic solvent at a solubility of at least 50 g/L; and
   c) removing the group A—L from the amino acid or peptide in a suitable organic solvent.

2. The process according to claim 1, wherein the group A is a bifunctional anchoring linker or spacer comprising at least one alcohol or amine function (B) and at the other end a carbonyl or ether function, wherein A is represented by the formula:

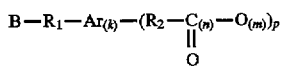

in which
B is a hydroxyl or amino group;
Ar is a mono- or polycyclic aromatic radical;
$R_1$ is selected from a covalent bond, an alkylene radical containing 1 to 4 carbon atoms, or an alkylenecarbonyl group and wherein said alkylene radical is unsubstituted or substituted with an aryl radical;
$R_2$ is selected from a covalent bond, an alkylene radical containing 1 to 4 carbon atoms, or an oxygen atom and wherein said alkylene radical is unsubstituted or substituted with an aryl radical;
k, m and n are integers equal to 0 or 1; m or n must be 1 and when m is equal to 1, n is 0 and when n is equal to 1, m is 0; and
p is an integer equal to 1 or 2.

3. The process according to claim 2, wherein the aromatic radical comprises a phenyl, biphenyl, terphenyl, naphthyl or anthracenyl group.

4. The process according to claim 3 wherein the activated carboxyl group is an acid chloride or an active ester, or wherein the activated carboxyl group is obtained by activation of a carboxyl group with a carbodiimide or with an alkyl chloroformate.

5. The process according to claim 1, wherein A—L is of one of the formulae:

B—R$_1$—Ar' or B—CH$_{(3-q)}$—Ar"$_{(q)}$ in which:

B represents a hydroxyl or amino group;

R$_1$ is selected from a covalent bond, an alkylene radical containing 1 to 4 carbon atoms, unsubstituted or substituted with a phenyl radical, and an alkylene carbonyl group;

Ar' is a polycyclic aromatic radical;

Ar" is a phenyl radical; and q is an integer equal to 2 or 3 with the proviso that the group A—L contains at least 18 carbon atoms.

6. The process according to claim 1 wherein P—COOH represents an amino acid selected from the group consisting of L-serine and L-leucine.

7. A process for temporarily rendering an amino acid soluble in a water-immiscible organic solvent comprising the steps of:

a) coupling, in a suitable organic solvent, an amino acid with a non-polymeric lipophilic substituent to form an amino acid reaction product Q—CO—A—L, according to the following reaction:

Q—COOH+A—L→Q—CO—A—L wherein

Q—COOH represents an amino acid, and

L represents a non-polymeric lipophilic group which bears a linking moiety A, subject to the proviso that A and L together contain at least 18 carbon atoms, and wherein said process the C-terminal carboxyl group of said amino acid is bonded via ester or amide linkage to the group A—L in the reaction product, and wherein said reaction product is soluble in said water-immiscible organic solvent to the extent of at least 50 g/L;

b) washing the amino acid reaction product of step (a) with a neutral, acidic, or basic aqueous solution while the amino acid reaction product remains dissolved in the water-immiscible organic solvent at a solubility of at least 50 g/L; and c) removing the group A—L from the amino acid reaction product.

8. A process for temporarily rendering L-serine soluble in a water-immiscible organic solvent comprising the steps of:

a) coupling, in a suitable organic solvent, the amino acid serine with a lipophilic group to form the seryl derivative Ser-A—L wherein L represents a non-polymeric lipophilic group which bears a linking moiety A, subject to the proviso that A and L together contain at least 18 carbon atoms, and wherein said process the carboxyl group of the serine is bonded via ester or amide linkage to the group A—L in the seryl derivative, and wherein the solubility of the seryl derivative is less than about 30 g/L in water at 25° C., b) washing the seryl derivative of step (a) with a neutral, acidic, or basic aqueous solution while the seryl derivative remains dissolved in the water-immiscible organic solvent at a solubility of at least 50 g/L; and c) removing the group A—L from the seryl derivative.

9. A process for the synthesis of a peptide in a liquid medium comprising the steps of:

a) coupling, in a water-immiscible organic solvent, an amino acid or peptide with a lipophilic substituent to form a reaction product P—CO—A—L, in conformance with the following reaction:

P—COOH+A—L→P—CO—A—L wherein

P—COOH represents an amino acid or peptide, and

L represents a non-polymeric lipophilic group which bears a linking moiety A, subject to the proviso that A and L together contain at least 18 carbon atoms, and wherein said process the C-terminal carboxyl group of said amino acid or peptide is bonded via ester or amide linkage to the group A—L in the reaction product, and wherein said reaction product is soluble in said water-immiscible organic solvent to the extent of at least 50 g/L;

b) coupling, in a water-immiscible organic solvent, an activated carboxyl group of a second peptide or amino acid P'—COOH with a free amino group of the reaction product from step (a);

c) washing the peptide reaction product of step (b) with a neutral, acidic, or basic aqueous solution while the peptide remains dissolved in the water-immiscible organic solvent at a solubility of at least 50 g/L;

d) repeating steps (b) and (c) until the desired amino acid sequence is obtained; and e) removing the group A—L from the peptide in a suitable organic solvent.

10. The process according to claim 9 wherein the N-terminal amino group of P'—COOH is protected prior to coupling step (b).

11. The process according to claim 9, wherein the water-immiscible organic solvent comprises a solvent selected from halogenated aliphatic derivatives, aromatic derivatives and esters.

12. The process according to claim 10 wherein reactive side chain moieties are also protected.

13. The process according to claim 10 wherein the N-terminal amino group is protected with a tert-butyloxycarbonyl (Boc) group or as a condensation product with a beta-dicarbonyl compound.

14. The process according to claim 9 wherein the activated carboxyl group is an acid chloride or an active ester, or wherein the activated carboxyl group is obtained by activation of a carboxyl group with a carbodiimide or with an alkyl chloroformate.

15. The process according to claim 1 or 9 wherein the linking moiety A is selected from the group consisting of

—O—CH$_2$—C$_6$H$_4$—CO—,

—O—CH$_2$—C$_6$H$_4$—CH$_2$—CO—,

—O—CH$_2$—C$_6$H$_4$—CH$_2$—CH$_2$—CO—,

—O—CH$_2$—CH(C$_6$H$_5$)—C$_6$H$_3$(D$^1$)(D$^2$)—,

—O—CH(C$_6$H$_5$)—C$_6$H$_3$(D$^1$)(D$^2$)—, and

—NH—CH(C$_6$H$_5$)—C$_6$H$_3$(D$^1$)(D$^2$)— wherein D$^1$ and D$^2$ are independently selected from the group consisting of

—O—, —C=O—, —CH$_2$—O——CH$_2$—CO——OCO—and H, with the proviso that D$^1$ and D$^2$ cannot simultaneously represent H.

16. The process according to claim 15 wherein L is selected from the group consisting of:

| | |
|---|---|
| —O—CH₂—C₆H₄—O—C₆H₅, | —CO—C₆H₄—CO—C₆H₄—OMe, |
| —O—CH₂—C₆H₄—C₆H₅, | —CO—CH(C₆H₅)₂, |
| —CH₂—C₆H₄—C₆H₅, | —CO—C₆H₃(CO—O—D⁴)₂, |
| —CH₂—C₆H₄—O—C₆H₅, | —CO—CH₂—C₁₀H₇, |
| —CH₂—C₆H₃(OD³)₂, | —CO—CH₂—O—C₆H₄—C₉H₁₉, |
| —CH₂—C₆H₃(O—CO—D³)₂, | —O—CH₂—C₆H₄—C₆H₅, |
| —C₆H₄—D³, | —O—CH₂—C₁₀H₇, |
| —C₆H₄—COO—D³, | —O—CH₂—C₆H₄—O—C₆H₅, |
| —CO—C₆H₃(O—CO—D³)₂, | —O—CH₂—CH₂—O—C₁₀H₇, |
| —O—CH₂—C₆H₄—OD³, | and —O—CH₂—C₆H₄—CO—C₆H₅, | wherein $C_{10}H_7$ represents a naphthyl moiety, $D^3$ is a $C_1$–$C_{12}$-alkyl group, and $D^4$ is an aryl or aralkyl group;

with the proviso that the group A—L contains at least 18 carbon atoms.

17. The process according to claim 16 wherein A—L is —O—CH₂—C₆H₄—CO—CH₂—C₆H₄—C₆H₅.

18. A process for the synthesis of a peptide in a liquid medium comprising the steps of:

a) coupling, in a water-immiscible organic solvent, an amino acid or peptide with a lipophilic substituent to form a reaction product P—CO—A—L, in conformance with the following reaction:

P—COOH+A—L→P—CO—A—L wherein

P—COOH represents an amino acid or peptide, and

L represents a non-polymeric lipophilic group which bears a linking moiety A, subject to the proviso that A and L together contain at least 18 carbon atoms, and wherein said process the C-terminal carboxyl group of said amino acid or peptide is bonded via ester or amide linkage to the group A—L in the reaction product, and wherein said reaction product is soluble in said water-immiscible organic solvent to the extent of at least 50 g/L;

b) coupling, in a water-immiscible organic solvent, an activated carboxyl group of an N-terminally protected peptide with a free amino group of the reaction product from step (a);

c) washing the peptide reaction product of step (b) with a neutral, acidic, or basic aqueous solution while the peptide remains dissolved in the water-immiscible organic solvent at a solubility of at least 50 g/L; and d) removing the group A—L from the peptide in a suitable organic solvent.

19. The process according to claim 18, wherein the water-immiscible organic solvent comprises a solvent selected from halogenated aliphatic derivatives, aromatic derivatives and esters.

20. The process according to claim 18 wherein the N-terminal amino group is protected with a tert-butyloxycarbonyl (Boc) group or as a condensation product with a beta-dicarbonyl compound.

21. A process for the synthesis of a peptide in a liquid medium comprising the steps of:

a) coupling the amino acid serine with a lipophilic group to form the seryl derivative Ser-A—L wherein L represents a non-polymeric lipophilic group which bears a linking moiety A, subject to the proviso that A and L together contain at least 18 carbon atoms, and wherein said process the carboxyl group of the serine is bonded via ester or amide linkage to the group A—L in the seryl derivative, and wherein the solubility of the seryl derivative is less than about 30 g/L in water at 25° C., b) coupling, in a water-immiscible organic solvent, an activated carboxyl group of a peptide or amino acid with the free amino group of the seryl derivative, c) washing the peptide reaction product of step (b) with a neutral, acidic, or basic aqueous solution while the peptide remains dissolved in the water-immiscible organic solvent at a solubility of at least 50 g/L; and d) removing the group A—L from the resulting peptide in a suitable organic solvent.

* * * * *